US008034353B2

(12) United States Patent
Yano et al.

(10) Patent No.: US 8,034,353 B2
(45) Date of Patent: Oct. 11, 2011

(54) PEPTIDE VACCINE FOR INDUCING THE PRODUCTION OF ANTI-AMYLOID β-PEPTIDE ANTIBODY

(75) Inventors: Akira Yano, Iwate (JP); Toshiki Nishizawa, Tokyo (JP); Yoshikatsu Miwa, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 418 days.

(21) Appl. No.: 12/280,535

(22) PCT Filed: Feb. 16, 2007

(86) PCT No.: PCT/JP2007/052828
§ 371 (c)(1),
(2), (4) Date: Aug. 22, 2008

(87) PCT Pub. No.: WO2007/097251
PCT Pub. Date: Aug. 30, 2007

(65) Prior Publication Data
US 2010/0062011 A1 Mar. 11, 2010

(30) Foreign Application Priority Data

Feb. 22, 2006 (JP) ................................. 2006-044808

(51) Int. Cl.
*A61K 39/02* (2006.01)
*A61K 39/04* (2006.01)
*A61K 39/05* (2006.01)
*A61K 39/08* (2006.01)
*C07H 21/04* (2006.01)

(52) U.S. Cl. ............. 424/197.11; 424/185.1; 424/190.1; 424/245.1; 424/247.1; 424/248.1; 536/23.4

(58) Field of Classification Search ........................ None
See application file for complete search history.

(56) References Cited

U.S. PATENT DOCUMENTS

| 7,241,606 B2 | 7/2007 | Kubota et al. |
| 7,309,696 B2 | 12/2007 | Kucera et al. |
| 2004/0247612 A1 | 12/2004 | Wang |
| 2005/0142132 A1 | 6/2005 | Schenk et al. |

FOREIGN PATENT DOCUMENTS

| EP | 1614695 A1 | 1/2006 |
| JP | 9514805 A | 2/2005 |
| WO | 9927944 A1 | 6/1999 |
| WO | 0210361 A1 | 2/2002 |
| WO | 02096350 A2 | 12/2002 |
| WO | 03015812 A2 | 2/2003 |
| WO | 03089460 A1 | 10/2003 |
| WO | 2004087767 A1 | 10/2004 |

OTHER PUBLICATIONS

Janus C et al. Abeta peptide immunization reduces behavioural impairment and plaques in a model of Alzheimer's disease. Nature, 2000; 408:979-982.*
Morgan D et al. Abeta peptide vaccination prevents memory loss in an animal model of Alzheimer's disease. Nature, 2000; 408:982-985.*
Schenk D et al. Immunization with amyloid-beta attenuates Alzheimer-disease-like pathology in the PDAPP mouse. Nature, 1999; 400:173-177.*
Solomon B. Immunological approaches as therapy for Alzheimer's disease. Expert Opin. Biol. Ther. 2002; 2(8):907-917.*
Vickers JC. A vaccine against Alzheimer's disease: Developments to date. Drugs Aging. 2002; 19(7):487-494.*
Agadjanyan et al., Prototype Alzheimer's disease vaccine using the immunodominant B cell epitope from beta-amyloid and promiscuous T cell epitope pan HLA DR-binding peptide, Journal Immunology, 174(3):1580-1586 (2005).
Singh et al., ProPred: prediction of HLA-DR binding sites, Bioinformatics, 17(12):1236-1237 (2001).
Yano, 9. Saibo Ketsugo Hairetsu o Mochiita Eki Kyushusei Peptide Seizai no Sekkei, Atarshii Iryo Kiki Kenkyu, 11:16 along with its excerpt translation (2006).
Yano et al., An ingenious design for peptide vaccines, Vaccine, 23:2322-2326 (2005).
M. Manea, et al., "Polypeptide Conjugates Comprising a β-Amyloid Plaque-Specific Epitope as New Vaccine Structures Against Alzheimer's Disease", Biopolymers (Peptide Science), Jan. 1, 2004, p. 503-511, vol. 76, No. 6, Wiley Periodicals, Inc.
M. Maier, et al., "Short Amyloid-β (Aβ) Immunogens Reduce Cerebral Aβ Load and Learning Deficits in an Alzheimer's Disease Mouse Model in the Absence of an Aβ-Specific Cellular Immune Response", The Journal of Neuroscience, May 3, 2006, p. 4717-4728, vol. 26, No. 18, Society of Neuroscience.

* cited by examiner

*Primary Examiner* — Elizabeth C Kemmerer
*Assistant Examiner* — Kimberly A Ballard
(74) *Attorney, Agent, or Firm* — Browdy and Neimark, PLLC

(57) ABSTRACT

An object of the present invention is to provide a peptide vaccine for preventing and/or treating diseases caused by amyloid β-peptide, such as Alzheimer's disease. The present invention solves the above object by providing a peptide vaccine constructed by inserting a peptide having an amino acid sequence of a cell attachment motif of a cell adhesive molecule to a peptide which consists of a peptide having an amino acid sequence of multiagretope type T-cell epitope, which has been generated immunological memory, or a peptide including the same; an linker peptide; and a peptide having an amino acid sequence of a B cell epitope which is a specific region of amyloid β-peptide or a peptide including the same.

4 Claims, No Drawings

SEQUENCE LISTING

<160> NUMBER OF SEQ ID NOS: 38

<210> SEQ ID NO 1
<211> LENGTH: 40
<212> TYPE: PRT
<213> ORGANISM: human
<223> OTHER INFORMATION: amyloid beta (1-40)

```
<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: human
<223> OTHER INFORMATION: amyloid beta (1-42)

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 20
<212> TYPE: PRT
<213> ORGANISM: artificial sequence
<220> FEATURE:
<223> OTHER INFORMATION: overlapping multiagretope peptide

<400> SEQUENCE: 3

Leu Ala Val Tyr Trp Glu Leu Leu Ala Lys Tyr Leu Leu Asp Arg Val
1               5                   10                  15

Gln Lys Val Ala
            20

<210> SEQ ID NO 4
<211> LENGTH: 15
<212> TYPE: PRT
<213> ORGANISM: human immunodeficiency virus
<223> OTHER INFORMATION: gag protein (partial sequence)

<400> SEQUENCE: 4

Lys Arg Trp Ile Ile Leu Gly Leu Asn Lys Ile Val Arg Met Tyr
1               5                   10                  15

<210> SEQ ID NO 5
<211> LENGTH: 11
<212> TYPE: PRT
<213> ORGANISM: human
<223> OTHER INFORMATION: amyloid beta (N-terminal partial sequence
      (1-11))

<400> SEQUENCE: 5

Asp Ala Glu Phe Arg His Asp Ser Gly Tyr Glu
1               5                   10

<210> SEQ ID NO 6
<211> LENGTH: 13
<212> TYPE: PRT
<213> ORGANISM: human
<223> OTHER INFORMATION: amyloid beta (N-terminal partial sequence
      (1-13))
```

```
<400> SEQUENCE: 6

Asp Ala Glu Phe Arg His Asp Ser Gly Tyr Glu Val His
1               5                   10

<210> SEQ ID NO 7
<211> LENGTH: 15
<212> TYPE: PRT
<213> ORGANISM: human
<223> OTHER INFORMATION: amyloid beta (N-terminal partial sequence
      (1-15))

<400> SEQUENCE: 7

Asp Ala Glu Phe Arg His Asp Ser Gly Tyr Glu Val His His Gln
1               5                   10                  15

<210> SEQ ID NO 8
<211> LENGTH: 9
<212> TYPE: PRT
<213> ORGANISM: human
<223> OTHER INFORMATION: amyloid beta (N-terminal partial sequence
      (3-11))

<400> SEQUENCE: 8

Glu Phe Arg His Asp Ser Gly Tyr Glu
1               5

<210> SEQ ID NO 9
<211> LENGTH: 13
<212> TYPE: PRT
<213> ORGANISM: human
<223> OTHER INFORMATION: amyloid beta (N-terminal partial sequence
      (3-15))

<400> SEQUENCE: 9

Glu Phe Arg His Asp Ser Gly Tyr Glu Val His His Gln
1               5                   10

<210> SEQ ID NO 10
<211> LENGTH: 20
<212> TYPE: PRT
<213> ORGANISM: Corynebacterium diphtheriae
<223> OTHER INFORMATION: diphtheria toxoid (partial sequence)

<400> SEQUENCE: 10

Ala Tyr Asn Phe Val Glu Ser Ile Ile Asn Leu Phe Gln Val Val His
1               5                   10                  15

Asn Ser Tyr Asn
            20

<210> SEQ ID NO 11
<211> LENGTH: 19
<212> TYPE: PRT
<213> ORGANISM: Corynebacterium diphtheriae
<223> OTHER INFORMATION: diphtheria toxoid (partial sequence)

<400> SEQUENCE: 11

Tyr Asn Phe Val Glu Ser Ile Ile Asn Leu Phe Gln Val Val His Asn
1               5                   10                  15

Ser Tyr Asn

<210> SEQ ID NO 12
<211> LENGTH: 16
<212> TYPE: PRT
<213> ORGANISM: Clostridium tenani
<223> OTHER INFORMATION: tetanus toxoid (partial sequence)
```

```
-continued

<400> SEQUENCE: 12

Leu Gln Thr Met Val Lys Leu Phe Asn Arg Ile Lys Asn Asn Val Ala
1               5                   10                  15

<210> SEQ ID NO 13
<211> LENGTH: 18
<212> TYPE: PRT
<213> ORGANISM: Clostridium tenani
<223> OTHER INFORMATION: tetanus toxoid (partial sequence)

<400> SEQUENCE: 13

Phe Leu Gln Thr Met Val Lys Leu Phe Asn Arg Ile Lys Asn Asn Val
1               5                   10                  15

Ala Gly

<210> SEQ ID NO 14
<211> LENGTH: 16
<212> TYPE: PRT
<213> ORGANISM: Clostridium tenani
<223> OTHER INFORMATION: tetanus toxoid (partial sequence)

<400> SEQUENCE: 14

Ile His Val Leu His Gly Leu Tyr Gly Met Gln Val Ser Ser His Glu
1               5                   10                  15

<210> SEQ ID NO 15
<211> LENGTH: 18
<212> TYPE: PRT
<213> ORGANISM: Clostridium tenani
<223> OTHER INFORMATION: tetanus toxoid (partial sequence)

<400> SEQUENCE: 15

Leu Ile His Val Leu His Gly Leu Tyr Gly Met Gln Val Ser Ser His
1               5                   10                  15

Glu Ile

<210> SEQ ID NO 16
<211> LENGTH: 18
<212> TYPE: PRT
<213> ORGANISM: Clostridium tenani
<223> OTHER INFORMATION: tetanus toxoid (partial sequence)

<400> SEQUENCE: 16

Tyr Ile Val Asn Glu Asp Lys Phe Gln Ile Leu Tyr Asn Ser Ile Met
1               5                   10                  15

Tyr Gly

<210> SEQ ID NO 17
<211> LENGTH: 20
<212> TYPE: PRT
<213> ORGANISM: Clostridium tenani
<223> OTHER INFORMATION: tetanus toxoid (partial sequence)

<400> SEQUENCE: 17

Gln Tyr Ile Val Asn Glu Asp Lys Phe Gln Ile Leu Tyr Asn Ser Ile
1               5                   10                  15

Met Tyr Gly Phe
            20

<210> SEQ ID NO 18
<211> LENGTH: 15
<212> TYPE: PRT
<213> ORGANISM: Clostridium tenani
<223> OTHER INFORMATION: tetanus toxoid (partial sequence)
```

```
<400> SEQUENCE: 18

Ser Tyr Gln Met Tyr Arg Ser Leu Glu Tyr Gln Val Asp Ala Ile
 1               5                  10                  15

<210> SEQ ID NO 19
<211> LENGTH: 16
<212> TYPE: PRT
<213> ORGANISM: Clostridium tenani
<223> OTHER INFORMATION: tetanus toxoid (partial sequence)

<400> SEQUENCE: 19

Arg Ser Tyr Gln Met Tyr Arg Ser Leu Glu Tyr Gln Val Asp Ala Ile
 1               5                  10                  15

<210> SEQ ID NO 20
<211> LENGTH: 15
<212> TYPE: PRT
<213> ORGANISM: Clostridium tenani
<223> OTHER INFORMATION: tetanus toxoid (partial sequence)

<400> SEQUENCE: 20

Asn Ile Asn Ile Phe Met Arg Glu Ser Ser Arg Ser Phe Leu Val
 1               5                  10                  15

<210> SEQ ID NO 21
<211> LENGTH: 17
<212> TYPE: PRT
<213> ORGANISM: Clostridium tenani
<223> OTHER INFORMATION: tetanus toxoid (partial sequence)

<400> SEQUENCE: 21

Ile Asn Ile Asn Ile Phe Met Arg Glu Ser Ser Arg Ser Phe Leu Val
 1               5                  10                  15

Asn

<210> SEQ ID NO 22
<211> LENGTH: 20
<212> TYPE: PRT
<213> ORGANISM: Mycobacterium tuberculosis
<223> OTHER INFORMATION: MPT64 (partial sequence)

<400> SEQUENCE: 22

Ile Gln Met Ser Asp Pro Ala Tyr Asn Ile Asn Ile Ser Leu Pro Ser
 1               5                  10                  15

Tyr Tyr Pro Asp
            20

<210> SEQ ID NO 23
<211> LENGTH: 16
<212> TYPE: PRT
<213> ORGANISM: Mycobacterium tuberculosis
<223> OTHER INFORMATION: MPT64 (partial sequence)

<400> SEQUENCE: 23

Ile Gln Met Ser Asp Pro Ala Tyr Asn Ile Asn Ile Ser Leu Pro Ser
 1               5                  10                  15

<210> SEQ ID NO 24
<211> LENGTH: 16
<212> TYPE: PRT
<213> ORGANISM: Mycobacterium tuberculosis
<223> OTHER INFORMATION: MPT64 (partial sequence)
```

```
<400> SEQUENCE: 24

Asp Pro Ala Tyr Asn Ile Asn Ile Ser Leu Pro Ser Tyr Tyr Pro Asp
1               5                   10                  15

<210> SEQ ID NO 25
<211> LENGTH: 16
<212> TYPE: PRT
<213> ORGANISM: Mycobacterium tuberculosis
<223> OTHER INFORMATION: MPT64 (partial sequence)

<400> SEQUENCE: 25

Tyr Asn Ile Asn Ile Ser Leu Pro Ser Tyr Tyr Pro Asp Gln Lys Ser
1               5                   10                  15

<210> SEQ ID NO 26
<211> LENGTH: 5
<212> TYPE: PRT
<213> ORGANISM: human
<223> OTHER INFORMATION: binding motif of cell adhesion molecule

<400> SEQUENCE: 26

Pro His Ser Arg Asn
1               5

<210> SEQ ID NO 27
<211> LENGTH: 4
<212> TYPE: PRT
<213> ORGANISM: human
<223> OTHER INFORMATION: binding motif of cell adhesion molecule

<400> SEQUENCE: 27

Asp Gly Glu Ala
1

<210> SEQ ID NO 28
<211> LENGTH: 5
<212> TYPE: PRT
<213> ORGANISM: human
<223> OTHER INFORMATION: binding motif of cell adhesion molecule

<400> SEQUENCE: 28

Tyr Ile Gly Ser Arg
1               5

<210> SEQ ID NO 29
<211> LENGTH: 5
<212> TYPE: PRT
<213> ORGANISM: human
<223> OTHER INFORMATION: binding motif of cell adhesion molecule

<400> SEQUENCE: 29

Ile Lys Val Ala Val
1               5

<210> SEQ ID NO 30
<211> LENGTH: 8
<212> TYPE: PRT
<213> ORGANISM: human
<223> OTHER INFORMATION: binding motif of cell adhesion molecule

<400> SEQUENCE: 30

Arg Phe Tyr Val Val Met Trp Lys
1               5
```

```
<210> SEQ ID NO 31
<211> LENGTH: 5
<212> TYPE: PRT
<213> ORGANISM: human
<223> OTHER INFORMATION: binding motif of cell adhesion molecule

<400> SEQUENCE: 31

Ile Arg Val Val Met
 1               5

<210> SEQ ID NO 32
<211> LENGTH: 29
<212> TYPE: PRT
<213> ORGANISM: artificial sequence
<220> FEATURE:
<223> OTHER INFORMATION: peptide for the production of anti-amyloid
      beta antibody

<400> SEQUENCE: 32

Arg Gly Asp Lys Arg Trp Ile Ile Leu Gly Leu Asn Lys Ile Val Arg
 1               5                  10                  15

Met Tyr Lys Lys Glu Phe Arg His Asp Ser Gly Tyr Glu
            20                  25

<210> SEQ ID NO 33
<211> LENGTH: 31
<212> TYPE: PRT
<213> ORGANISM: artificial sequence
<220> FEATURE:
<223> OTHER INFORMATION: peptide for the production of anti-amyloid
      beta antibody

<400> SEQUENCE: 33

Arg Gly Asp Lys Arg Trp Ile Ile Leu Gly Leu Asn Lys Ile Val Arg
 1               5                  10                  15

Met Tyr Lys Lys Asp Ala Glu Phe Arg His Asp Ser Gly Tyr Glu
            20                  25                  30

<210> SEQ ID NO 34
<211> LENGTH: 33
<212> TYPE: PRT
<213> ORGANISM: artificial sequence
<220> FEATURE:
<223> OTHER INFORMATION: peptide for the production of anti-amyloid
      beta antibody

<400> SEQUENCE: 34

Arg Gly Asp Lys Arg Trp Ile Ile Leu Gly Leu Asn Lys Ile Val Arg
 1               5                  10                  15

Met Tyr Lys Lys Asp Ala Glu Phe Arg His Asp Ser Gly Tyr Glu Val
            20                  25                  30

His

<210> SEQ ID NO 35
<211> LENGTH: 38
<212> TYPE: PRT
<213> ORGANISM: artificial sequence
<220> FEATURE:
<223> OTHER INFORMATION: peptide for the production of anti-amyloid
      beta antibody
```

-continued

```
<400> SEQUENCE: 35

Arg Gly Asp Ala Tyr Asn Phe Val Glu Ser Ile Ile Asn Leu Phe Gln
1               5                   10                  15

Val Val His Asn Ser Tyr Asn Lys Lys Asp Ala Glu Phe Arg His Asp
            20                  25                  30

Ser Gly Tyr Glu Val His
        35

<210> SEQ ID NO 36
<211> LENGTH: 38
<212> TYPE: PRT
<213> ORGANISM: artificial sequence
<220> FEATURE:
<223> OTHER INFORMATION: peptide for the production of anti-amyloid
      beta antibody

<400> SEQUENCE: 36

Arg Gly Asp Gln Tyr Ile Val Asn Glu Asp Lys Phe Gln Ile Leu Tyr
1               5                   10                  15

Asn Ser Ile Met Tyr Gly Phe Lys Lys Asp Ala Glu Phe Arg His Asp
            20                  25                  30

Ser Gly Tyr Glu Val His
        35

<210> SEQ ID NO 37
<211> LENGTH: 38
<212> TYPE: PRT
<213> ORGANISM: artificial sequence
<220> FEATURE:
<223> OTHER INFORMATION: peptide for the production of anti-amyloid
      beta antibody

<400> SEQUENCE: 37

Arg Gly Asp Ile Gln Met Ser Asp Pro Ala Tyr Asn Ile Asn Ile Ser
1               5                   10                  15

Leu Pro Ser Tyr Tyr Pro Asp Lys Lys Asp Ala Glu Phe Arg His Asp
            20                  25                  30

Ser Gly Tyr Glu Val His
        35

<210> SEQ ID NO 38
<211> LENGTH: 36
<212> TYPE: PRT
<213> ORGANISM: artificial sequence
<220> FEATURE:
<223> OTHER INFORMATION: peptide for the production of anti-amyloid
      beta antibody

<400> SEQUENCE: 38

Arg Gly Asp Phe Leu Gln Thr Met Val Lys Leu Phe Asn Arg Ile Lys
1               5                   10                  15

Asn Asn Val Ala Gly Lys Lys Asp Ala Glu Phe Arg His Asp Ser Gly
            20                  25                  30

Tyr Glu Val His
        35
```

US 8,034,353 B2

PEPTIDE VACCINE FOR INDUCING THE PRODUCTION OF ANTI-AMYLOID β-PEPTIDE ANTIBODY

TECHNICAL FIELD

The present invention relates to a peptide having a good immunogenicity, which efficiently induces the production of antibodies specific to human amyloid β-peptide (hereinafter, abbreviated as "Aβ"), a composition comprising the peptide as an effective ingredient, and use thereof, more particularly, to a peptide efficiently inducing the production of antibodies against a specific B-cell epitope of Aβ and a composition for preventing and/or treating neurodegenerative diseases represented by Alzheimer's disease, comprising the peptide as an effective ingredient.

BACKGROUND ART

In aging advanced countries, agnostic patients go on increasing and the increase becomes recognized as a serious problem. Agnosia is classified into cerebrovascular agnosia, caused by cerebrovascular disease, and Alzheimer's disease. Alzheimer's disease is known as a large part of the cause of developing senile agnosia and deteriorates QOL (Quality of Life) of the patients because it gives rise to memory disorder and movement disorder. Alzheimer's disease requires considerable nursing care in addition to the treatment of the disease and also raises the cost of health care and social burdens such as time loss, loss of working opportunity and psychological burden of the patients, their families and care-givers. Alzheimer's disease is one of serious neurodegenerative diseases with no fundamental treating method. The pathologic characteristics of the disease are the deposition of "senile plaque", i.e., the accumulation of Aβ consisting of 40 (SEQ ID NO:1) or 42 (SEQ ID NO:2) amino acid residues to central nerve, the neurofibrillary degeneration and the degeneration and deficiency of nerve cells. For treating Alzheimer's disease, the treatment using cholinesterase inhibitor and clinical trials using cholesterol-lowering agent and cerebral nerve-protective agent such as ethyl-EPA are carried out.

Also, expecting the permanent cure, the development of vaccines for preventing the target molecule, Aβ which is a major cause of Alzheimer's disease, is now in progress (Rf. Agadjanyan M. G. et al., *Journal of Immunology*, Vol. 174, No. 3. pp. 1580-1586 (2005)). In addition, the development of human anti-Aβ monoclonal antibodies, DNA vaccines, novel adjuvants such as CpGDNA, and peptide vaccines for oral administration is also in progress. However, DNA vaccines are restricted by major histocompatibility antigen (hereinafter, abbreviated as "MHC") class I and tend to induce the activation of cytotoxic T-cell. Peptide vaccines have low immunogenicity and require adjuvant for inducing antibodies because they defect the ability of inducing antibodies against Aβ. When the antigen has a relatively high molecular weight, the immunological reaction to the epitopes has a possibility of causing unexpected inflammatory responses because the antigen has many T-cell or B-cell epitopes. Further, the inflammatory responses give a risk of causing encephalitis as a side effect. Therefore, the fundamental treating method for Alzheimer's disease has not been established yet. Although Aβ is known to involve in the development and progression of various diseases except for Alzheimer's disease, the preventing method and treating method for those diseases have not been established yet.

To overcome those problems, the present inventors disclosed that a peptide vaccine; designed to have an amino acid sequence of cell attachment motif in a peptide which is designed to have an amino acid sequence including T-cell epitope at the amino terminus, linker peptide, and an amino acid sequence including B-cell epitope at the carboxyl terminus; can be used for inducing the production of antibodies specific to Aβ and for treating Alzheimer's disease (Ref. International Patent Application No. WO 2004/87767). However, the specific amino acid sequence of the peptide vaccine usable to overcome the problems is not described in the specification of International Patent Application No. WO 2004/87767. Further, it was revealed that the overlapping-shift-type multiagretope peptide (SEQ ID NO:3, hereinafter, abbreviated as "OMP") and a peptide (SEQ ID NO:4, hereinafter, abbreviated as "Gag") having an amino acid sequence of the 298th to 312nd of Gag protein originated from human immunodeficiency virus (hereinafter, abbreviated as "HIV"), described in International Patent Application No. WO 2004/87767, have low activities for inducing the production of antibodies specific to Aβ when they are used as T-cell epitopes. For inducing the production of antibodies specific to Aβ in many patients of Alzheimer's disease as possible, it is necessary to design a T-cell epitope which is restricted by many human MHC class II haplotypes, i.e., HLA (human leucocyte antigen)-DR haplotypes (allele) as possible and is able to induce the production of antibodies specific to Aβ strongly. As a peptide vaccine used for preventing and/or treating Alzheimer's disease and other various neurodegenerative diseases, it is desired that the peptide is able to inhibit the progress of symptoms rapidly, to induce the production of antibodies specific to Aβ effectively by low administration frequency as possible from the viewpoint of economical cost, and has a smaller risk to induce serious side-effects when it is administered to human.

DISCLOSURE OF INVENTION

An object of the present invention is to provide a peptide vaccine for preventing and/or treating various diseases such as neurodegenerative diseases represented by Alzheimer's disease, caused by Aβ.

To solve the above object, the present inventors have been extensively studied. As a result, it was found that a peptide vaccine, having the strong activity of inducing the production of antibodies specific to a B-cell epitope in the absence of adjuvant, can be prepared by using the immunological memory which has been already acquired in human, i.e., by preliminary administrating a peptide including a T-cell epitope or selecting a T-cell epitope included in a sensitized antigen peptide such as an inactivated vaccine used for vaccination and a toxin. Further, it was found that a peptide having an amino acid sequence of cell attachment motif in cell adhesive molecule in a peptide designed to be connecting the above-mentioned T-cell epitope peptide and a B-cell epitope peptide having a specific region of Aβ via a linker peptide can be used for effectively inducing the production of antibodies which recognize a specific region of Aβ by the transmucosal administration using transnasal or oral pathway. Furthermore, it was found that a peptide having a specific amino acid sequence can be used for effectively inducing the production of antibodies which recognize a specific region of Aβ in many persons with avoiding the problem of HLA-DR restriction by using a multiagretope-type epitope restricted by multiple HLA-DR as the T-cell epitope. Based on the above knowledge, the present inventors accomplished the present invention.

The present invention provides a peptide, having an amino acid sequence represented by the following General Formula, which efficiently induces the production of antibodies specific to Aβ and a composition for preventing and/or treating various diseases such as neurodegenerative diseases represented by Alzheimer's disease.

$$R_1\text{-}T\text{-}R_2\text{-}L\text{-}R_3\text{-}B\text{-}R_4 \quad \text{General Formula}$$

(wherein the symbol "T" means an amino acid sequence including an amino acid sequence of T-cell epitope which has been generated immunological memory; the symbol "L" means an amino acid sequence of a linker peptide; the symbol "B" means an amino acid sequence including one or more amino acid sequences of B-cell epitope of Aβ; and at least one of the symbols "$R_1$", "$R_2$", "$R_3$" and "$R_4$" is an amino acid sequence of a cell attachment motif peptide of a cell adhesive molecule.)

BEST MODE FOR CARRYING OUT THE INVENTION

"The peptide for inducing the production of antibodies specific to Aβ" as referred to as in the present invention means the peptide having an amino acid sequence represented by General Formula, which has an ability of inducing the production of antibodies against B-cell epitope of Aβ or an amino acid sequence including the same.

The term "antibody" as referred to as in the present invention means mainly immunoglobulin G (IgG), immunoglobulin M (IgM), and immunoglobulin A (IgA), and includes those secreted intranasally, orally, orbitally and intestinally as well as in the blood and the body fluid.

"The disease caused by Aβ" as referred to as in the present invention means a disease caused by deposition of Aβ to specific tissues and includes diseases that the deposition is the main cause, diseases accompanied with other diseases, which are generated or exacerbated by the deposition of Aβ, and clinical symptoms accompanied by those diseases. Specifically, diseases caused by Aβ includes Alzheimer's disease, Pick's disease, diffuse Lewy bodies disease, progressive supranuclear palsy (Steele-Richardson disease), multisystem atrophy (Shy-Drager syndrome), amyotrophic lateral sclerosis, degenerative ataxia, cortical base degeneration, Guamanian ALS-Parkinson-dementia complication, subacute sclerosing panencephalitis, Huntington's chorea, Parkinson's disease, synucleinopathy, primary progressive aphasia, striatonigral degeneration, motor neuron disease including Machado-Joseph disease/spinal corebellare degeneration type 3 and olivo-ponto-cerebellar atrophy, Gilles de la Tourette's syndrome, bulbar palsy and pseudobulbar palsy, spinal and spinobulbar amylotrophia (Kennedy's syndrome, primary funiculus lateralis scleroma, familial spastic paraplegia, Werdnig-Hoffmann disease, Kugelberg-Welander disease, Tay-Sachs disease, Sandhoff's disease, familial spasmodic disease, Wohlfahrt-Kugelberg-Welander disease, spastic paraplegia, progressive multifocal white matter cerebral disorder, prion disease (Creutzfeldt-Jakob disease), Gerstmann-Straussler-Scheinker disease, dementia caused by increasing age including kuru disease and lethal familial insomnia, vascular dementia, diffusion white matter disease (Binswanger's disease), dementia caused by endocrine or metabolism, dementia caused by head injury and diffusion cerebral injury, demented fighting pose or frontal lobe dementia; neurodegenerative disease caused by infarct including cerebral ischemia, embolic and thrombotic infarct, and arbitrary intracerebral hemorrhage; intracerebral injury and vertebral injury; hereditary cerebral angiopathy; non-neuropathic hereditary amyloid; Down's syndrome; macroglobulinemia; secondary familial Mediterranean fever; Muckle-Wells syndrome; multiple myeloma; amyloidosis related to disease of pancreas or cardiac affection; chronic hemodialysis arthropathia or Finland-type and Iowa-type amyloidosis; neurodegenerative disease such as diabetic neuropathy; diabetes caused by deposition of Aβ to pancreas; and clinical symptoms accompanied by those diseases.

The B-cell epitope of Aβ, used as a site for inducing the production of antibodies in the peptide vaccine of the present invention, is a peptide including an amino acid sequence of B-cell epitope of Aβ which is recognized as the cause of Alzheimer's disease. As such B-cell epitope, desired is a peptide having an amino acid sequence capable of inducing antibodies, which induces the dissolution of agglutinated fibrae of Aβ or inhibits the deposition of Aβ to neurofibrae and other organs or the binding of Aβ to acetylcholine receptor. From the viewpoint, a peptide having an amino acid sequence of amino terminal region of Aβ is preferable. In addition, a peptide consisting 5 to 20 amino acid residues is preferable. If the number of amino acid residues contained in the B-cell epitope is too small, the activity of inducing the production of antibodies is disappeared. If the number is too large, its antigenicity is increased, however, the epitope has a possibility of inducing antibodies which cause side-effects. The peptide including the B-cell epitope can be used directly or after making into a dimmer, trimer or polymer by connecting the same in tandem arrangement. If necessary, two or more different B-cell epitopes present on Aβ can be used by connecting them in tandem arrangement. Further, the whole of Aβ, i.e., Aβ consisting of 40 amino acid residues (SEQ ID NO:1, hereinafter, abbreviated as "Aβ(1-40)") or that consisting of 42 amino acid residues (SEQ ID NO:2, hereinafter, abbreviated as "Aβ(1-42)") can be used as the B-cell epitope. A peptide, inducing multiple antibodies simultaneously, can be arbitrarily designed by connecting multiple epitopes. In such case, each epitope can be processed surely by inserting linker peptide(s) described later between the B-cell epitopes.

In the case of using an amino acid sequence of the amino terminal region of Aβ as B-cell epitope, the peptide must have the 4th to 10th amino acid sequence from the amino terminus of Aβ. As such peptides, for example, a peptide having an amino acid sequence of DAEFRHDSGYE, the 1st to 11th of the amino acid sequence of SEQ ID NO:1 or 2 (SEQ ID NO:5, hereinafter abbreviated as "Aβ(1-11)"); that having an amino acid sequence of DAEFRHDSGYEVH, the 1st to 13th of the same (SEQ ID NO:6, hereinafter abbreviated as "Aβ(1-13)"); that having an amino acid sequence of DAEFRHDSGYEVHHQ, the 1st to 15th of the same (SEQ ID NO:7, hereinafter abbreviated as "Aβ(1-15)"); that having an amino acid sequence of EFRHDSGYE, the 3rd to 11th of the same (SEQ ID NO:8, hereinafter abbreviated as "Aβ(3-11)"); that having an amino acid sequence of EFRHDSGYEVHHQ, the 3rd to 15th of the same (SEQ ID NO:9, hereinafter abbreviated as "Aβ(3-15)"); and etc. can be used. From the viewpoint of the ability of inducing the production of antibodies specific to Aβ and side effects, Aβ(1-13) or Aβ(1-15) can be preferably used. More preferably, Aβ(1-13) can be used.

The T-cell epitope used in the peptide vaccine of the present invention is a T-cell epitope of an antigen that the immunological memory has been generated in the objective subject, when the peptide vaccine of the present invention is administered. Such immunological memory can be generated by preliminary administrating a peptide including the same T-cell epitope with the peptide vaccine of the present invention to the patient to be administered the peptide vaccine of the present invention. Particularly, the T-cell epitope of antigen protein that the immunological memory has been generated in the majority of human after early childhood by vaccination can be used without the above procedure of generating immunological memory. Also, further positive effect is expectable by applying the above procedure to the patient who has already acquired such immunological memory. Since a T-cell epitope is restricted by HLA-DR haplotypes and present as an antigen for helper T-cell, it is preferable to use the overlapping-shift type multiagretope peptide restricted by many HLA-DR haplotypes and a peptide including the same as the T-cell epitope. Peptides used as antigens for vaccination for, for example, diphtheria, tetanus, pertussis, inflammation of sublingual gland, rubella, measles, tuberculosis, etc., are desirable as the T-cell epitope used in the present invention because the immunological memories have been generated in the majority of human from the early childhood. Particularly, T-cell epitopes originated from tetanus toxoid, diphtheria toxoid, pertussis vaccine, and tuberculosis vaccine are desirable from the viewpoint of versatility because the inoculation of diphtheria pertussis tetanus vaccine and BCG vaccine is imposed in Japan and carried out worldwide. Since the amino acid sequences of those toxoids or vaccines are well-known, the known T-cell epitope sequences of those peptides can be used as the T-cell epitope in the present invention. Further, the T-cell epitope sequence in the antigen peptide can be identified by testing the blastgenesis of peripheral blood of human, and then the T-cell epitope can be used in the present invention. Furthermore, the amino acid sequence of the T-cell epitope can be determined by predicting multiagretope region capable of binding to many HLA-DR using a T-cell epitope-predicting program. From the viewpoint of side-effects, it is preferable that the T-cell epitope has a low activity of inducing the production of antibodies specific to the epitope. However, since the T-cell epitope is inherently used for inducing the production of antibodies specific to the epitope, the safety of the antibodies specific to the T-cell epitope has been confirmed because of using the T-cell epitope originated from the sensitized antigen used for vaccination even if the production of antibodies specific to the T-cell epitope is induced. Therefore, the T-cell epitope used in the present invention has a merit of hardly causing side-effects. The T-cell epitope can be used directly or in the form that the same or different T-cell epitopes are bound tandemly. The T-cell epitope is capable of exhibiting the function even though amino acid residues except for those constructing agretope (amino acid residues required for binding to HLA-DR antigen) are substituted with other amino acid residues.

As such T-cell epitope, for example, a peptide having an amino acid sequence of AYNFVESIINLFQVVHNSYN (SEQ ID NO:10) and that having an amino acid sequence of NYFVESIINLFQVVHNSYN (SEQ ID NO:11) (hereinafter abbreviated as "DTL" and "DTS19", respectively), which are epitopes derived from diphtheria toxoid; a peptide having an amino acid sequence of LQTMVKLFNRIKNNVA (SEQ ID NO:12), that having an amino acid sequence of FLQTMVKLFNRIKNNVAG (SEQ ID NO:13), that having an amino acid sequence of IHVLHGLYGMQVSSHE (SEQ ID NO:14), that having an amino acid sequence of LIHVLHGLYGMQVSSHEI (SEQ ID NO:15), that having an amino acid sequence of YIVNEDKFQILYNSIMYG (SEQ ID NO:16), that having an amino acid sequence of QYIVNEDKFQILYNSIMYGF (SEQ ID NO:17), that having an amino acid sequence of SYQMYRSLEYQVDAI (SEQ ID NO:18), that having an amino acid sequence of RSYQMYRSLEYQVDAI (SEQ ID NO:19), that having an amino acid sequence of NINIFMRESSRSFLV (SEQ ID NO:20), and that having an amino acid sequence of ININIFMRESSRSFLVN (SEQ ID NO:21) (hereinafter, abbreviated as "TetT1", "TetT1L", "TetT2", "TetT2L", "TetT3", TetT3L", "TetT4", "TetT4L", "TetT5", and "TetT5L", respectively), which are epitopes derived from tetanus toxoid; a peptide having an amino acid sequence of IQMSDPAYNINISLPSYYPD (SEQ ID NO:22), that having an amino acid sequence of IQMSDPAYNINISLPS (SEQ ID NO:23), that having an amino acid sequence of DPAYNINISLPSYYPD (SEQ ID NO:24), and that having an amino acid sequence of YNINISLPSYYPDQKS (SEQ ID NO:25) (hereinafter, abbreviated as "MptL(43-62)", "MptN (43-58)", "MptM(47-62)", and "MptC(50-65)", respectively, which are epitopes derived from MPT64 known as a common secretion protein of *Mycobacterium tuberculosis/bovis*. Among them, MptL(43-62), DTL, TetT1L and TetT3L were predicted to be able to bind with 47 allele, 39 allele, 41 allele, and 50 allele, respectively, in 51 allele enable to bind with HLA-DR, predicted by "ProPrep", a HLA-DR restriction-predicting program described later. Also, since they have strong activity of inducing the production of antibodies, they can be preferably used as the T-cell epitope. DTL can be more preferably used.

If necessary, the presence of the memory T-cell can be confirmed by the steps of culturing the T-cell epitope and peripheral blood of a subject to be administered with the peptide vaccine of the present invention and detecting the blastogenesis, or detecting the delayed-type hypersensitivity (DTH) by intradermally administrating the small amount of the peptide vaccine. Based on the above results, the T-cell epitope suitable to the objective subject can be arbitrarily selected.

The linker peptide used for linking a peptide including B-cell epitope and that including T-cell epitope is not restricted as far as it is a recognition site of a protease involved in antigen processing. As such linker peptides, dipeptides such as lysine-lysine (KK), lysine-arginine (KR), and arginine-arginine (RR) can be used. Among them, the dipeptide, lysine-lysine which is a recognition site of cathepsin B can be preferably used.

Any cell attachment motif of cell adhesive molecule can be used in the present invention as far as it has a function of allowing the peptide of the present invention to stay on the surface of the mucous membranes for a long period and enhances the activity of inducing the production of antibodies by the administration though transmucosal pathway such as oral and transnasal pathway. For example, amino acid sequences of cell attachment motif to integrin family and other cell attachment motifs can be used. As cell attachment motif belonging to the integrin attachment motif, peptides having amino acid sequences of arginine-glycine-aspartic acid (hereinafter, abbreviated as "RGD"), arginine-glutamic acid-aspartic acid (hereinafter, abbreviated as "RED"), leucine-aspartic acid-valine (hereinafter, abbreviated as "LDV"), proline-histidine-serine-arginine-asparagine ("PHSRN", SEQ ID NO:26), arginine-lysine-lysine ("RKK"), and asparagic acid-glycine-glutamic acid-alanine ("DGEA", SEQ ID NO:27), which are known as cell attachment motifs existing on cell adhesive molecules such as fibronectin, collagen, vitronectin, fibrinogen, laminin, Tat protein of human immunodeficiency virus (HIV), can be used. As the cell attachment motif other than integrin family, peptides having amino acid sequences of tyrosine-isoleucine-glycine-serine-arginine ("YIGSR", SEQ ID NO:28), isoleucine-lysine-valine-alanine-valine ("IKVAV", SEQ ID NO:29), arginine-phenylalanine-tyrosine-valine-valine-methionine-tryptophane-lysine ("RFYVVMWK", SEQ ID NO:30), and isoleucine-arginine-valine-valine-methionine ("IRVVM", SEQ ID NO:31) can be used. Among them, peptides having amino acid sequences of RGD, RED, or YIGSR are preferable because they strongly induce the production of specific antibodies. More preferably, a peptide, RGD can be used. The position, where those peptides having the amino acid sequences of cell attachment motif should be inserted, can be selected from four positions, i.e., amino terminus or carboxyl terminus of the T-cell epitope peptide or the B-cell epitope peptide, and one or more positions can be used. It is preferable to insert at amino terminus and/or carboxyl terminus of T-cell epitope peptide because the resulting peptide specifically enhances the production of antibodies specific to the B-cell epitope peptide. The peptide that the cell attachment motif is inserted to the amino terminus of the T-cell epitope peptide is more preferable.

The method for producing the peptide of the present invention is not specifically restricted. The peptide can be prepared by a usual peptide synthesizing method. Optionally, the peptide can be prepared by connecting peptides which are partially synthesized before by a usual peptide synthesizing method. Also, the peptide can be synthesized using a peptide synthesizer commercialized by various manufacturers according to the attached protocols. Further, the peptide can be prepared according to conventional recombinant DNA techniques. For example, the peptide can be prepared by the steps of; preparing a DNA encoding the an amino acid sequence of the designed peptide; inserting the resulting DNA into a self-replicable vector; and introducing the resulting recombinant DNA into a host, i.e., microorganisms such as *E. coli, Bacillus subtilis, Actinomycete*, and yeast, animals, plants, cells or tissues thereof to prepare transformant; or generating the transgenic animals or plants; culturing or breeding the resultants; and collecting or purifying the peptide of the present invention by arbitrary methods. Optionally, the peptide of the present invention can be prepared by the steps of; expressing a polypeptide that the peptide of the present invention is connected with the same using a digestion site of protease other than that used for connecting T-cell epitope and B-cell epitope; and digesting the resulting polypeptides with the proteases. The microorganisms, animals, or plants, expressed the peptides of the present invention, can be arbitrarily used after processing directly into a composition for oral use, comprising the peptide of the present invention. As such plants, for example, plants belonging Asteraceae, Brassicaceae, Cucurbitaceae, , Rosaceae, Vitaceae, Vaccinium, Caricaceae, Fabaceae, Juglandaceae, Chenopodiaceae, Solanaceae, Convolvulaceae, Poaceae, and Dioscoreaceae can be used. More specifically, lettuce, chicory, tansy, broccoli, cabbage, radish, horseradish, pepper, cucumber, melon, pumpkin, chayote, carrot, hornwort, celery, apple, plum, apricot, peach, strawberry, raspberry, almond, pear, Japanese medlar, grape, cranberry, blaeberry, blueberry, papaya, alfalfa, soybean, walnut, spinach, tomato, paprika, sweet potato, rice pant, maize, wheat, barley, rye, Japanese yam, potato, etc. can be used. The peptide of the present invention can be directly prepared by any method described before. Also, the peptide of the present invention can be arbitrarily prepared by chemically connecting peptides having the partial amino acid sequences, synthesized preliminary.

The peptide of the present invention can be advantageously made into a composition in combination with one or more pharmaceutically acceptable ingredients as far as the effect of the present invention is not inhibited. Such pharmaceutically acceptable ingredient includes solvents such as water and alcohols; reducing saccharides such as glucose, maltose, trehalose and sucrose; non-reducing saccharides such as α,α-trehalose, saccharide-derivatives of α,α-trehalose such as α-maltosyl maltose, a cyclic tetrasaccharide having a structure of cyclo-{→6)-α-D-glucopyranosyl-(1→3)-α-D-glucopyranosyl-(1→6)-α-D-glucopyranosyl-(1→3)-α-D-glucopyranosyl-(1→} disclosed in International Patent Application No. WO 02/10361 applied for by the same applicant of the present invention, a cyclic tetrasaccharide having a structure of cyclo{→6)-α-D-glucopyranosyl-(1→4)-α-D-glucopyranosyl-(1→6)-α-D-glucopyranosyl-(1→4)-α-D-glucopyranosyl-(1→} disclosed in Japanese Patent Kokai No. 95140/2005, and cyclodextrins; sugar alcohols such as sorbitol, mannitol, maltitol, and maltotriitol; water-soluble polymers such as agar, pullulan, Guar gum, and Arabic gum; proteins such as gelatin and silk; hydrolyzates of protein, lipids, amino acids, buffering agent, stabilizing agent, antimicrobial agent, flavors, nutritional functional foods, effective ingredients of medicated cosmetics and pharmaceuticals; immunological adjuvant such as alum and aluminum hydroxide; and other food ingredients and pharmaceutical additives. One or more ingredients describe above can be arbitrarily used in combination. Among them, α,α-trehalose, saccharide-derivatives of α,α-trehalose and cyclic tetrasaccharides can be preferably used because they exhibit the effect of stabilizing the peptide.

The form of the agent comprising the peptide of the present invention is not specifically restricted as far as the peptide in the agent can be sustained stably for a long period. The form can be arbitrarily selected from the group consisting of solution, freeze-dried product, tablet, sublingual tablet, troche, powder, granule, cream, ointment, and syrup in consideration of administration subject, method of administration, preservation method of the agent, and transport method. The peptide of the present invention or a composition comprising the same can be advantageously impregnated to the position of antigen presenting cells by enclosing it into liposome or using in combination with an impregnation-promoting agent to skin and tissues and iontophoresis method. The peptide of the present invention can be arbitrarily administered through transmucosal pathway by incorporating into various foods and beverages such as tablet confectionary, candy, soft drink, etc. and administrating orally. The peptide of the present invention can be expressed in the living body by the method called "gene therapy" which directly administrates the RNA encoding the peptide of the present invention to the living body or introduces the DNA into cells.

The administration method of the peptide of the present invention or the composition comprising the same to human is not restricted to a specific one as long as it surely transports the peptide to the desired position. For example, it can be dropped on mucosae with a dropper or syringe, ingested orally, applied on mucosae after formed in a cream or gel form, introduced into the desired position with a catheter, sprayed after formed in a mist form with a spray or nebulizer, or aspirated into the nose, trachea, or lung. An administration method using a syringe, catheter, or intravenous drip can be used when the peptide is administered subcutaneously, intracutaneously, intramuscularly, intravascularly, and intracoelarly such as intraperitoneally and intrapleurally. Varying depending on the activity of inducing antibody, kind of disease, administration pathway, administration method, and animal to be administered; a dose of the peptide of the present invention is usually 0.00001 to 100 mg/kg-body weight, preferably, 0.0001 to 25 mg/kg-body weight, more preferably, 0.001 to 10 mg/kg-body weight. In addition, since the peptide of the present invention is able to induce the production of antibodies specific to Aβ efficiently by the first administration, the production of the antibodies specific to Aβ can be enhanced even in the case of using a peptide having the amino acid sequence of B-cell epitope only of the peptide of the present invention as a booster.

The following experiments explain the peptide of the present invention in more detail.

Experiment 1

Effect of B-cell Epitope on the Production of Antibodies Specific to Aβ

An experiment for investigating the effect of B-cell epitope on the production of antibodies specific to Aβ was carried out as follows.

Preparation of a Peptide for Inducing the Production of Antibodies

A peptide having an amino acid sequence of the 298th to 312th of Gag protein (SEQ ID NO:4) derived from HIV-1 (hereinafter, abbreviated as "Gag") was used as T-cell epitope. Three peptides, Aβ(1-11) (SEQ ID NO:5) having an amino acid sequence of the 1st to 11th from the amino terminus of Aβ (SEQ ID NO:1 or 2), Aβ(1-13) (SEQ ID NO:6) having an amino acid sequence of the 1st to 13th of Aβ, and Aβ (3-11) (SEQ ID NO:8) having an amino acid sequence of the 3rd to 11th of Aβ were used as B-cell epitope. Three peptides shown in Table 1, i.e., RGD-Gag-KK-Aβ(3-11) (SEQ ID NO:32), RGD-Gag-KK-Aβ(1-11) (SEQ ID NO:33), and RGD-Gag-KK-Aβ(1-13) (SEQ ID NO:34) were synthesized by connecting a cell attachment motif, arginine-glycine-aspartic acid (RGD) to the amino terminus of the T-cell epitope, connecting a linker, lysine-lysine (KK) to the carboxyl terminus of the resultant, and connecting a B-cell epitope, any one of Aβ(1-11), Aβ(1-13), and Aβ(3-11), to the carboxyl terminus of the resultant, and then used as antigens in the experiment. The peptide described in the present specification is synthesized by Fmoc method using "Model 350 MULTIPLE PEPTIDE SYNTHESIZER", a peptide synthesizer produced by Advanced Chemtech, and purified to give a purity of 95% or higher by reverse-phase HPLC using "TSK-GEL" (i.d.: 1 cm, length: 30 cm), a column produced by Tosoh Corporation, Tokyo, Japan; or that obtained by consigning the synthesis to SIGMA Genosys in Sigma Aldrich Japan (purity of the peptide: about 95%).

Vaccination of Mice and the Determination of Antibody Titer

The above peptides were administered to five-week aged BALB/c female mice (commercialized by Japan SLC Co. Ltd., Tokyo, Japan; five mice/group) transnasally, and then the concentrations of anti-Gag antibodies and anti-Aβ antibodies (antibody titer) in the blood of respective mouse were determined. For the vaccination, any one of the peptide was administered to the mice with a dose of 50 μg/mouse/once and totally four times at two weeks interval. After one week from the last administration, the blood was collected from the respective mouse and the antibody titers of anti-Gag antibodies and anti-Aβ antibodies in the serum were determined by the conventional ELISA using Gag or Aβ (SEQ ID NO:2) as a coating antigen. The results are in Table 1. The antibody titers to the respective antigen, described in the present specification, were determined as follows: the antisera prepared from the blood collected from the respective mouse were serially diluted 2-folds and placed in microtiter plates to be subjected to measuring the concentration of antibodies by ELISA method using enzyme-labeled antibodies, and then, the resulting plates were subjected to measuring the absorbance at 405 nm of each well using "MULTISCAN Bichromatech", a microtiter plate reader commercialized by Labosystem Corporation. The antibody titers were calculated by averaging the maximum dilution values showing that the difference between the absorbance at 405 nm of well coated with the antigen and that of well uncoated control is 0.1 or higher. The antiserum from the mouse not being vaccinated was used as negative control.

TABLE 1

| Peptide used for vaccination | Mice used for vaccination | Antibody titer Anti-Gag antibody | Anti-Aβ antibody |
|---|---|---|---|
| RGD-Gag-KK-Aβ(3-11) | BALB/c | 16 | 22.6 |
| RGD-Gag-KK-Aβ(1-11) | BALB/c | 11.3 | 14.9 |
| RGD-Gag-KK-Aβ(1-13) | BALB/C | 12.1 | 32 |
| None | BALB/c | 5.7 | 9.2 |

As is evident from Table 1, three peptides used for vaccination showed low antigenicities. Those antibody titers of antibodies against Gag used as T-cell epitope were 11 to 16. Those antibody titers of antibodies against Aβ used as B-cell epitope were 14.9 to 32. In both cases, the antibody titers were low, i.e., about 2 to 3-folds of that of non-vaccinated serum (Control), and indistinguishable with the background level. Therefore, from the results of this experiment system, those peptides were considered to be not preferable for inducing the production of antibodies specific to Aβ.

Experiment 2

Effect of the Memory T-cell on the Production of Antibodies Specific to Aβ

An experiment for investigating the effect of the memory T-cell on the production of antibodies specific to Aβ was carried out as follows. In Experiment 1, the induction of the production of antibodies by the T-cell epitope and the B-cell epitope cannot be detected and indistinguishable with the background level. Then, after inducing the memory T-cell specific to the T-cell epitope, mice were vaccinated using the peptides of the present invention and the antibody titers in the serum of mice were determined by the same method in Experiment 1. Considering the application of the peptides of the present invention to human, it is impractical to induce the memory T-cell specific to an antigen, that human is not usually sensitized, such as Gag. Therefore, T-cell epitopes derived from tetanus toxoid and diphtheria toxoid that the majority of the adult have acquired the immunologic memory by vaccination and has the memory T-cell were used in this experiment. T-cell epitope sequences in those toxoids were determined by predicting the multiagretope region using "ProPrep", a known HLA-DR restriction predicting program (Ref. Singh H. and Raghava G. P. S., "ProPrep: prediction of HLA-DR binding sites.", *Bioinfomatics*, Vol. 17, pp. 1236-1237, 2001), and selected DTL from diphtheria toxoid and TetT3L from tetanus toxoid as T-cell epitopes. It was preliminary confirmed that any peptide having those T-cell epitope sequences can be used for inducing the blastogenesis of the T-cell by the mixed cultivation with peripheral blood from three mice or three persons different in HLA-DR haplotypes. By the above experiment, it was confirmed that the peptides having those T-cell epitope sequences were multiagretopes against mice and human. Therefore, the peptides were used for the experiment.

Preparation of Peptides for Inducing the Production of Antibodies

Two peptides, having the same amino acid sequences with peptides used in Experiment 1 except for using DTL or TetT3L as T-cell epitope and Aβ(1-13) as B-cell epitope, i.e., RGD-DTL-KK-Aβ(1-13) (SEQ ID NO:35) and RGD-TetT3L-KK-Aβ(1-13) (SEQ ID NO:36) were synthesized.

Vaccination of Mice and the Determination of Antibody Titer

At one week before of administrating above peptides, 50 μl of tetanus and diphtheria binary mixed vaccine (produced by The Chemo-Sero-Therapeutic Research Institute, Kumamoto, Japan; comprising 50 Lf/ml of diphtheria toxoid and about 80 μg/ml or lower of tetanus toxoid) was administrated subcutaneously to BALB/c female mice (commercialized by Japan SLC Co. Ltd., Tokyo, Japan; five mice/group) for inducing memory T-cells against tetanus toxoid and diphtheria toxoid. Then, any one of the above peptides was administered transnasally to the mice with a dose of 50 μg/mouse/once and totally four times at two weeks interval. After one week from the 4th administration, the blood was collected from the respective mouse and the antibody titers of anti-DTL antibodies, anti-TetT3L antibodies, and anti-Aβ antibodies in the blood were determined according to the method described in Example 1. The results are in Table 2. As controls, mice were treated by the same method without administrating binary mixed vaccine, and the antibody titers in the blood were determined by the same method and are also in Table 2. A peptide having the amino acid sequence of DTL, TetT3L, or Aβ was respectively used as a coating antigen for determining the antibody titers.

TABLE 2

| Peptide used for vaccination | Preliminary administration of binary mixed vaccine | Antibody titer | | |
|---|---|---|---|---|
| | | Anti-DTL antibody | Anti-TetT3L-antibody | Anti-Aβ antibody |
| None | None | 3 | 3 | 3 |
| RGD-DTL-KK-Aβ(1-13) | None | 5 | ND | 148 |
| RGD-TetT3L-KK-Aβ(1-13) | None | ND | 374 | 17 |
| RGD-DTL-KK-Aβ(1-13) | Administered | 11 | ND | 9561 |
| RGD-TetT3L-KK-Aβ(1-13) | Administered | ND | 787 | 445 |

Different from the results in Experiment 1, as is evident from Table 2, all peptides used for vaccination efficiently induced the production of antibodies specific to Aβ in mice. In the cases of being induced the memory T-cell against the T-cell epitope of each peptide by preliminary administrating the binary mixed vaccine, the antibody titers were increased to about 64-folds when the T-cell epitope derived from diphtheria toxiod (DTL) was used, and about 26-folds when the T-cell epitope derived from tetanus toxoid was used, in comparison with the cases of the binary mixed vaccine was not administrated. In the case of using DTL as the T-cell epitope, the production of anti-DTL antibodies was not practically induced. In the case of using TetT3L as the T-cell epitope, the antibody titer of anti-TetT3L antibodies was increased because TetT3L is also deemed to be a B-cell epitope in mice, however, the increase was mere 2-folds in comparison with the case of not administrating the binary mixed vaccine. While, the antibody titer of anti-Aβ antibodies can be increased by using a peptide designed to connect two or more Aβ(1-13) as the B-cell epitope. In addition, in the case of substituting Aβ(1-13) to Aβ(1-15), Aβ(3-11) or Aβ(3-15), almost the same results were obtained.

The results of the experiment indicate that the production of the antibodies specific to Aβ can be effectively enhanced by preliminary administrating an epitope that the memory T-cell has been present in the living body by vaccination, or a peptide including the same before administrating the peptide of the present invention. Further, the results of the experiment indicate that the activity of inducing the production of antibodies specific to the B-cell epitope of the peptide used for the sensitization can be enhanced by preliminary inducing the memory T-cell of the T-cell epitope of the peptide used for the sensitization in the living body. The results also indicate that DTL is preferable as the T-cell epitope because of low production of antibodies specific to the T-cell epitope. Depending on the MHC class II haplotypes, a T-cell epitope may be deemed as a B-cell epitope as in the case of the peptide using TetT3L as the T-cell epitope. In the cases of usual peptide vaccines, the induction of antibodies against an epitope except for the objective epitope increases a risk of causing side-effects. However, since the T-cell epitope is inherently used for inducing the production of antibodies specific to the epitope, the problem by the side-effects is not caused as far as using the T-cell epitope having an amino acid sequence of the peptides used for the vaccination even though the production of antibodies specific to the T-cell epitope is induced. Since the fact has been already confirmed, it is considered that the safety of the peptide of the present invention is very high.

The following examples explain the present invention more specifically, however, the present invention must not be restricted by them. In the following examples, the amount of each component was expressed by the percentage in the total amount of the objective composition if not otherwise specified.

EXAMPLE 1

Composition for Enhancing the Production of Antibodies Specific to Aβ

A peptide having an amino acid sequence of RGD-IQMS-DPAYNINISLPSYYPD-KK-DAEFRHDSGYEVH (SEQ ID NO:37), prepared according to the method in Experiment 1 using a T-cell epitope (MptL(43-62)) derived from MPT, a secreted protein of tuberculosis bacteria, and Aβ(1-13); and α,α-trehalose (reagent grade, commercialized by Hayashibara Biochemical Laboratories Inc., Okayama, Japan) were dissolved into distilled water to give concentrations of 100 μg/ml and 40%, respectively, and then sterilized by the conventional method. The resulting syrup was placed by 2 ml into sterilized vials, and sealed to make into a syrupy agent comprising the peptide. Since the product is stable and restricted by various HLA-DR haplotypes, it exerts the effect of vaccine which efficiently enhances the production of antibodies specific to Aβ, having the effect of preventing or treating various diseases such as neurodegenerative disease represented by Alzheimer's disease by administrating to human, particularly, tuberculin converter by transnasal or oral pathway. In the case of concatenating two or more Aβ(1-13), the production of the antibody can be enhanced. Further, in the case of substituting Aβ(1-13) to Aβ(1-15), Aβ(3-11), or Aβ(3-15), almost the same effect can be obtained.

EXAMPLE 2

Composition for Enhancing the Production of Antibodies Specific to Aβ

A peptide having an amino acid sequence of RGD-AYN-FVESIINLFQVVHNSYN-KK-DAEFRHDSGYEVH (SEQ ID NO:35), prepared according to the method in Experiment 1 using a T-cell epitope (DTL) derived from diphtheria toxoid and Aβ(1-13), was dissolved into physiological saline containing 1% (w/v) sucrose as a stabilizer to give concentrations of 10 μg/ml, 100 μg/ml or 1,000 μg/ml, and then sterilized by filtration. The resulting solution was placed by 1 ml into sterilized vials, freeze dried by the conventional method and sealed to make into an agent comprising the peptide. The product is used after dissolved in 1 ml of distilled water for injection. Since the product is stable and restricted by various HLA-DR haplotypes, it exerts the effect of vaccine which efficiently enhances the production of antibodies specific to Aβ, having the effect of preventing or treating various diseases such as neurodegenerative disease represented by Alzheimer's disease by administrating to human, particularly, human vaccinated against diphtheria by transnasal or oral pathway. In the case of concatenating two or more Aβ(1-13), the production of the antibody can be enhanced. Further, in the case of substituting Aβ(1-13) to Aβ(1-15), Aβ(3-11), or Aβ(3-15), almost the same effect can be obtained.

EXAMPLE 3

Safety Test for the Composition for Enhancing the Production of Antibodies Specific to Aβ

The peptide prepared in Example 1 or 2 was diluted with physiological saline containing 0.5% sucrose to give a concentration of 12.5 mg/ml, and then the dilute was administered to five week-aged DDY male mice by oral, interperitoneal, or intramuscular pathway to investigate $LD_{50}$ of the peptides. As the results, the $LD_{50}$ of the both peptides was 100 mg (peptide weight)/kg-mouse body weight or higher. The results indicate that the peptides of the present invention are safe preparations with no toxicity when administered to human.

EXAMPLE 4

Composition for Enhancing the Production of Antibodies Specific to Aβ

A physiological saline containing 150 μg/ml of a peptide having an amino acid sequence of RGD-FLQTMVKLFN-RIKNNVAG-KK-DAEFRHDSGYEVH (SEQ ID NO:38), prepared according to the method in Experiment 1 using a T-cell epitope (TetT1L) derived from tetanus toxoid and Aβ(1-13), and 100 mg/ml of mannitol was prepared. The resulting solution was placed by 1 ml into 5-ml vials and freeze dried by the conventional method. The product is used after dissolved in 1 ml of distilled water for injection. Since the product is stable and restricted by various HLA-DR haplotypes, it exerts the effect of vaccine which efficiently enhances the production of antibodies specific to Aβ, having the effect of preventing or treating various diseases such as neurodegenerative disease represented by Alzheimer's disease by administrating to human, particularly, human vaccinated against tetanus by transnasal or oral pathway. In the case of concatenating two or more Aβ(1-13), the production of the antibody can be enhanced. Further, in the case of substituting Aβ(1-13) to Aβ(1-15), Aβ(3-11), or Aβ(3-15), almost the same effect can be obtained.

EXAMPLE 5

Composition for Enhancing the Production of Antibodies Specific to Aβ

A physiological saline containing 75 μg/ml of a peptide having an amino acid sequence of RGD-QYIVNEDKFQI-LYNSIMYGF-KK-DAEFRHDSGYEVH (SEQ ID NO:36), prepared according to the method in Experiment 1 using a T-cell epitope (TetT3L) derived from tetanus toxoid and Aβ(1-13), and 0.5 mg/ml of human albumin was prepared. The resulting solution was placed by 1 ml into 5-ml vials and freeze dried by the conventional method. The product is used after dissolved in 1 ml of distilled water for injection. Since the product is stable and restricted by various HLA-DR haplotypes, it exerts the effect of vaccine which efficiently enhances the production of antibodies specific to Aβ, having the effect of preventing or treating various diseases such as neurodegenerative disease represented by Alzheimer's disease by administrating to human, particularly, human vaccinated against tetanus by transmucosal or transdermal pathway. In the case of concatenating two or more Aβ(1-13), the production of the antibody can be enhanced. Further, in the case of substituting Aβ(1-13) to Aβ(1-15), Aβ(3-11), or Aβ(3-15), almost the same effect can be obtained.

INDUSTRIAL APPLICABILITY

As described above, the present invention relates to the peptide including amino acid sequences of T-cell epitope which has been generated immunological memory in human and B-cell epitope of amyloid β-peptide, or a peptide including the same, which enables specifically to enhance the production of antibodies specific to Aβ in the absence of immunological adjuvant. Since the peptide of the present invention is restricted by various HLA-DR haplotypes, it can be used as a peptide vaccine which induces the production of antibodies specific to Aβ, having the effect of preventing or treating various diseases such as neurodegenerative disease represented by Alzheimer's disease by administrating to human, particularly, human being generated immunological memory by vaccination. The peptide vaccine of the present invention can be used without immunological adjuvant and through transmucosal pathway such as transnasal and oral pathway. Therefore, the peptide vaccine of the present invention is easy to use and safe in comparison of a vaccine administered by transdermal injection.

The present invention, having these outstanding effects, is a significant invention that greatly contributes to the art.

The invention claimed is:

1. A peptide, comprising an amino acid sequence represented by the following general formula $R_1$-T-$R_2$-L-$R_3$-B-$R_4$;

wherein the symbol "T" means an amino acid sequence consisting of a T-cell epitope amino acid sequence selected from the group consisting of SEQ ID NO:10, SEQ ID NO:13, SEQ ID NO:17, and SEQ ID NO:22; the symbol "L" means a linker peptide amino acid sequence; the symbol "B" means an amino acid sequence comprising one or more B-cell epitope amino acid sequences of amyloid β-peptide; and the symbols "$R_1$", "$R_2$", "$R_3$" and "$R_4$" mean one or more positions where an amino acid sequence(s) of cell attachment motif peptides of cell adhesive molecules can be located.

2. A composition for inducing the production of anti-amyloid β-peptide antibodies by transmucosal administration, comprising the peptide of claim 1 and one or more pharmaceutically acceptable ingredients.

3. The composition of claim 2 treating Alzheimer's disease.

4. A DNA, which encodes the peptide of claim 1.

* * * * *